United States Patent [19]
Pfeifer et al.

[11] Patent Number: 5,795,993
[45] Date of Patent: Aug. 18, 1998

[54] ACOUSTIC-WAVE SENSOR FOR AMBIENT MONITORING OF A PHOTORESIST-STRIPPING AGENT

[75] Inventors: Kent B. Pfeifer, Los Lunas; Andrea E. Hoyt, Albuquerque; Gregory C. Frye, Cedar Crest, all of N. Mex.

[73] Assignee: Sandia Corporation, Albuquerque, N. Mex.

[21] Appl. No.: 564,764

[22] Filed: Nov. 29, 1995

[51] Int. Cl.$^6$ .................................................. G01N 29/02
[52] U.S. Cl. ............................................ 73/24.01; 73/590
[58] Field of Search ................................ 73/24.01, 24.04, 73/24.06, 590, 584, 579; 310/313 B, 313 D, 313 R

[56] References Cited

U.S. PATENT DOCUMENTS

| | | | |
|---|---|---|---|
| 4,055,072 | 10/1977 | Fletcher | 73/23 |
| 4,312,228 | 1/1982 | Wohltjen | 73/597 |
| 4,847,594 | 7/1989 | Stetter | 340/540 |
| 4,895,017 | 1/1990 | Pyke | 73/579 |
| 4,932,255 | 6/1990 | Brace | 73/24.03 |
| 5,012,668 | 5/1991 | Haworth | 73/24.06 |
| 5,076,094 | 12/1991 | Frye | 73/24.04 |
| 5,117,146 | 5/1992 | Martin | 310/313 R |
| 5,224,972 | 7/1993 | Frye | 55/18 |
| 5,235,235 | 8/1993 | Martin | 310/313 D |
| 5,571,944 | 11/1996 | Pfeifer | 73/24.04 |

OTHER PUBLICATIONS

J.W. Grate and M.H. Abraham, *Solubility Interactions and the Design of Chemically Selective Sorbent Coatings for Chemical Sensors and Arrays*, Naval Research Laboratory Report No. 6692, 1990, Jul.

G. C. Frye, S.J. Martin, R. W. Cernosek, and K. B. Pfeifer, "Portable Acoustic Wave Sensor Systems for On–Line Monitoring of Volatile Organics," *International Journal of Environmentally Conscious Manufacturing*, vol. 1, pp. 37–45, 1992, (no month).

S.J. Patrash and E. T. Zellers, "Characterization of Polymeric Surface Acoustic Wave Sensor Coatings and Semiemperical Models of Sensor Responses to Organic Vapors, "*Analytical Chemistry*, vol. 65, pp. 2055–2066, Aug. 1, 1993.

K. B. Pfeifer, J. L. Sprung, and T. R. Galloway, "Polymer–Coated Surface Acoustic Wave Monitoring of CC14 in a Steam Reforming Reactor," *Sensors and Actuators B*, vol. 22, pp. 37–45, 1994, (no month).

*Primary Examiner*—Christine K. Oda
*Attorney, Agent, or Firm*—John P. Hohimer

[57] ABSTRACT

The acoustic-wave sensor. The acoustic-wave sensor is designed for ambient or vapor-phase monitoring of a photoresist-stripping agent such as N-methylpyrrolidinone (NMP), ethoxyethylpropionate (EEP) or the like. The acoustic-wave sensor comprises an acoustic-wave device such as a surface-acoustic-wave (SAW) device, a flexural-plate-wave (FPW) device, an acoustic-plate-mode (APM) device, or a thickness-shear-mode (TSM) device (also termed a quartz crystal microbalance or QCM) having a sensing region on a surface thereof. The sensing region includes a sensing film for sorbing a quantity of the photoresist-stripping agent, thereby altering or shifting a frequency of oscillation of an acoustic wave propagating through the sensing region for indicating an ambient concentration of the agent. According to preferred embodiments of the invention, the acoustic-wave device is a SAW device; and the sensing film comprises poly(vinylacetate), poly(N-vinylpyrrolidinone), or poly(vinylphenol).

15 Claims, 3 Drawing Sheets

ACOUSTIC-WAVE SENSOR FOR AMBIENT MONITORING OF A PHOTORESIST-STRIPPING AGENT

This invention was made with Government support under Contract No. DE-AC04-94AL85000 awarded by the U.S. Department of Energy. The Government has certain rights in the invention.

FIELD OF THE INVENTION

The present invention relates generally to acoustic-wave sensors, and more particularly to an acoustic-wave sensor for measuring an ambient concentration of a low-volatility photoresist-stripping agent such as N-methylpyrrolidinone (NMP), ethoxyethylpropionate (EEP) or the like within an integrated circuit facility or proximate to an exhaust stack thereof.

BACKGROUND OF THE INVENTION

Fabrication of integrated circuits (ICs) requires a precise control of many different parameters including the ambient atmosphere within an IC facility for minimizing contamination of semiconductor wafers and a consequent diminished yield of functional ICs. IC manufacturers have been largely concerned with particulate contamination. However, as feature sizes become smaller, manufacturers are becoming more concerned with molecular contamination. A particular area of concern is the contamination of photoresist-coated wafers by low-volatility organic vapors of photoresist-stripping agents such as N-methylpyrrolidinone (also termed 1-methyl-2-pyrrolidinone or NMP), ethoxyethylpropionate (also termed ethyl-3-ethoxypropionate or EEP) or the like which are used for photoresist-stripping process steps. Contamination of photoresist-coated wafers by a photoresist-stripping agent (prior to a photoresist-stripping process step) may soften the photoresist, thereby affecting device features patterned therein. Furthermore, monitoring of an ambient concentration of a photoresist-stripping agent within the IC facility or proximate to an exhaust stack thereof is important for worker protection and for control and monitoring of environmental releases, respectively.

The use of air sampling and a subsequent off-site analysis of ambient concentrations of photoresist-stripping agents has been practiced by the IC industry and may be useful for determining a degradation of granular activated carbon filters; but, such off-site analysis is disadvantageous in requiring a prolonged analysis time which makes it very difficult to determine a timing and/or source of release of the agents, and in being potentially costly in terms of a reduced yield of functional ICs. What is needed is an on-line, real-time monitor for ambient concentrations of photoresist-stripping agents for use in IC facilities. Such a real-time monitor may be used to detect period upset concentrations of photoresist-stripping agents in selected areas of the IC facility (including exhaust stacks) to alert workers of potential contamination or release problems so that a predetermined course of action may be taken in response thereto.

An advantage of the acoustic-wave sensor for monitoring an ambient concentration of one or more photoresist-stripping agents according to the present invention is that the sensor provides a high sensitivity of less than one part-per-million with an equilibrium response time of about two minutes.

Another advantage of the acoustic-wave sensor of the present invention is that the sensor may be tailored to provide a chemical selectivity for a particular photoresist-stripping agent by providing a sensing film in the sensor that has a selective sorbability for that particular photoresist-stripping agent.

These and other advantages of the acoustic-wave sensor of the present invention will become evident to those skilled in the art.

SUMMARY OF THE INVENTION

Accordingly, it is a primary object of the present invention to provide an acoustic-wave sensor for monitoring and quantifying an ambient concentration of one or more photoresist-stripping agents.

An additional object of the present invention is to provide an acoustic-wave sensor having a sensing film therein which selectively absorbs vapors from one or more photoresist-stripping agents and alters a frequency of oscillation of the sensor, thereby providing an indication of the ambient concentration of the photoresist-stripping agents.

A further object of the present invention is to provide an acoustic-wave sensor having a reversible response (i.e. selectively sorbing and desorbing vapors from one or more photoresist-stripping agents) so that the sensor may be used for long-term monitoring with continuous or intermittent sampling and/or readout.

Additional objects, advantages, and novel features of the invention will become apparent to those skilled in the art upon examination of the following description, or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as described herein, an acoustic-wave sensor is provided which according to embodiments thereof comprises an acoustic-wave device such as a surface-acoustic-wave (SAW) device, a flexural-plate-wave (FPW) device, an acoustic-plate-mode (APM) device, a thickness-shear-mode (TSM) device (also termed a quartz crystal microbalance or QCM) or the like having a sensing region on a surface thereof, with the sensing region including a sensing film for sorbing a quantity of the photoresist-stripping agent (PSA) and thereby altering or shifting a frequency of an acoustic wave propagating through the sensing region for indicating an ambient concentration of the photoresist-stripping agent.

According to a preferred embodiment of the present invention, the acoustic-wave device is a SAW device comprising a substrate; a pair of transducers on the substrate in a spaced relationship, a first transducer of the pair generating an acoustic wave which is propagated to a second transducer of the pair for detection thereof; an PSA sensing film on a surface of the substrate in a sensing region located between the pair of transducers, the sensing film sorbing a quantity of the photoresist-stripping agent proportional to a vapor-phase concentration thereof and thereby altering a frequency of oscillation of the acoustic wave, with the altered frequency providing an indication of the concentration of the vapor-phase photoresist-stripping agent.

The acoustic-wave sensor according to the present invention may further include electrical means connected to the acoustic-wave device for activating the device (i.e. generating one or more acoustic waves), and for sensing or measuring a frequency shift or alteration thereof. In some preferred embodiments of the present invention, the electrical means may include amplifying means for receiving the altered or shifted frequency of oscillation from one transducer in the sensor and providing an amplified feedback signal to another transducer in the sensor at the altered or shifted frequency of oscillation; and frequency detection means connected to the amplifying means for measuring the altered or shifted frequency of oscillation.

Other objects, advantages and novel features of the invention will become apparent from the following detailed description thereof when considered in conjunction with the accompanying drawings.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE INVENTION

Figure 1:
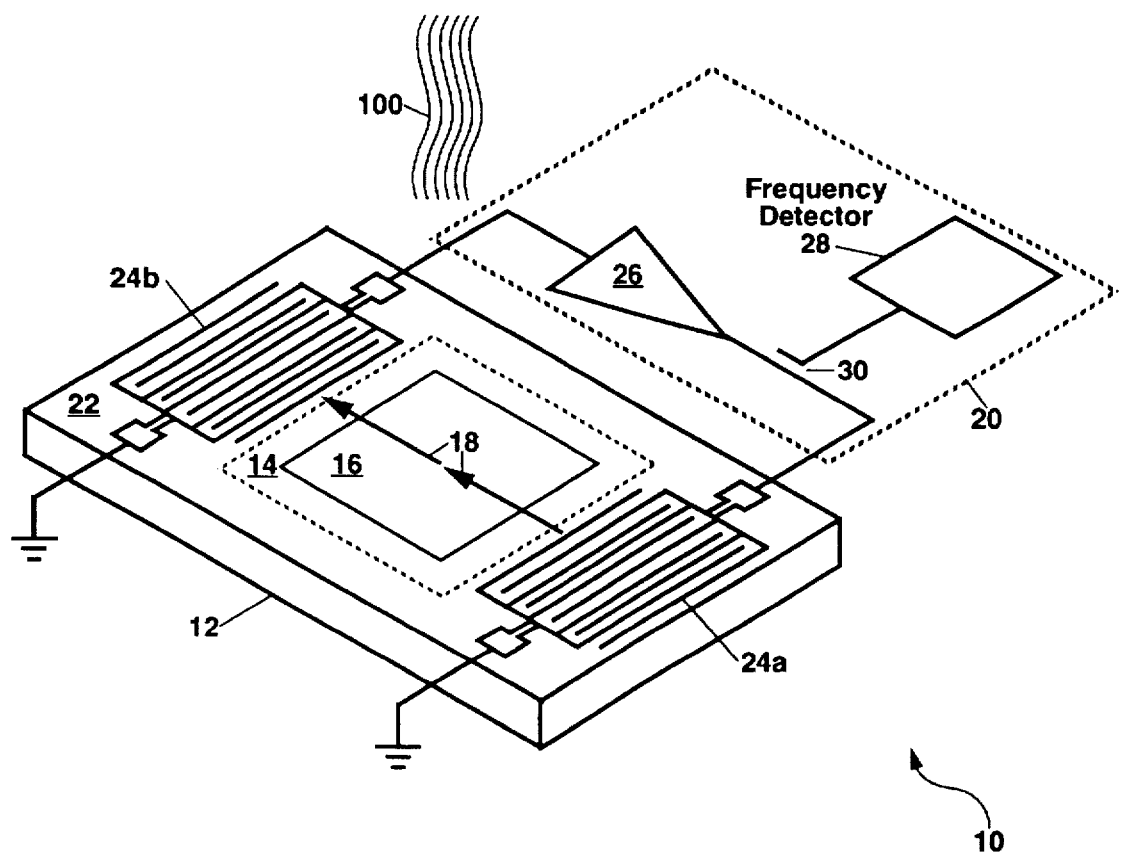
FIG. 1 shows an enlarged schematic in perspective of a preferred surface-acoustic wave (SAW) sensor embodiment of the present invention.

Referring to FIG. 1, there is shown an enlarged schematic in perspective of a preferred embodiment of the acoustic-wave sensor 10 according to the present invention. The acoustic-wave sensor 10 comprises an acoustic-wave device 12 having a sensing region 14 on a surface thereof. The sensing region 14 includes a photoresist-stripping-agent (PSA) sensing film 16 on the surface for sorbing (i.e. absorbing and/or adsorbing) a quantity of the PSA 100 (from an ambient or vapor-phase concentration in contact with the sensor 10, with the PSA being a low-volatility chemical species having a room-temperature vapor pressure of about 1 torr or less). Sorption of the PSA by the sensing film acts to shift or alter a frequency of an acoustic wave 18 propagating through the sensing region, with the frequency shift providing an indication or measure of the ambient concentration of the PSA 100. The acoustic-wave sensor 10 in FIG. 1 also preferably includes electrical means 20 connected to the acoustic-wave device for generating the acoustic wave, and for sensing the frequency shift or alteration thereof.

Acoustic-wave sensors use piezoelectric crystals in combination with conductive electrodes to couple electric fields and mechanical motion, thereby generating and detecting acoustic waves. Such acoustic-wave sensors are therefore sensitive to mass and mechanical properties (e.g. viscoelasticity) of a thin chemically-interactive sensing film formed on or attached to the acoustic-wave device 12, thereby allowing chemical species to be selectively sorbed (i.e. adsorbed and/or absorbed) and desorbed for altering the mass and properties of the film and affecting the acoustic waves therein.

In the preferred embodiment of the invention shown in FIG. 1, the acoustic-wave device 12 comprises a surface-acoustic-wave (SAW) device. The use of a SAW device is generally preferred for gas-phase and materials-characterization applications where no liquid contacts an exposed surface of the device, and where a maximum mass sensitivity is desired. For other embodiments of the present invention, other types of acoustic-wave devices 12 as known to the art may be used including flexural-plate-wave (FPW) devices, acoustic-plate-mode (APM) devices, and thickness-shear mode (TSM) devices. Furthermore, although only a single acoustic-wave device 12 is shown in FIG. 1, it will be understood that one or more additional acoustic-wave devices may be used for the acoustic-wave sensor to detect a plurality of different photoresist-stripping agents, or to provide a reference acoustic-wave device to provide a reference frequency for accurately determining the frequency shift and to compensate for environmental factors including temperature and humidity.

The SAW device 12 in FIG. 1 preferably comprises a generally rectangular substrate 22 and a pair of transducers (24a and 24b) on the substrate in a spaced relationship, and with the sensing region 14 (generally about 1 cm$^2$ or less) being located between the pair of transducers. The substrate 22 is preferably formed of a piezoelectric material such as crystalline quartz, lithium niobate, barium titanate, lithium tantalate or the like. In some cases, the substrate may comprise a piezoelectric coating material such as ZnO or AlN applied to a non-piezoelectric material such as silicon. In the preferred embodiment of the present invention shown in FIG. 1, the substrate is a polished single crystal of ST-cut quartz having a thickness of about 0.5 millimeters. (For embodiments of the present invention employing a TSM sensor 10, an alternating voltage applied to two opposite electrodes on a TSM device 12, typically comprising an AT-cut quartz substrate with electrodes on both sides thereof, induces a thickness-shear mode acoustic wave whose frequency of oscillation changes in proportion to mass changes in a sensing film 16 applied within a sensing region 14 on one or both surfaces of the device.)

In FIG. 1, the pair of transducers are formed at opposite ends of the substrate by depositing and photolithographically patterning a metallization (e.g. about 2 nanometers of Cr followed by about 200 nanometers of Au) on the substrate and forming a pair of interdigital electrodes, with each interdigital electrode being connected to a bond pad or the like for making electrical connections to the electrode Each interdigital electrode is comprised of a plurality of conductors (i.e. fingers) spaced at predetermined regular intervals of about 100 to 6 µm to provide an unperturbed frequency of oscillation, $f_0$, that is generally in the range of about 30–500 MHz. Further details on SAW devices for use in the present invention may be found in U.S. Pat. Nos. 5,076,094; 5,117,146; and 5,235,235 which are incorporated herein by reference.

In FIG. 1, a first transducer 24a of the pair, upon application of an alternating voltage thereto, generates an alternating strain field in the device due to the piezoelectric nature of the substrate. The alternating mechanical strain field launches one or more acoustic waves 18 in the general direction of the arrows in FIG. 1. If the acoustic wave travels along the surface of the substrate, the wave is termed a surface acoustic wave (SAW); and if the wave travels through the bulk of the substrate, the wave is termed an acoustic plate mode (APM). When the acoustic wave has significant amplitude at the surface, its propagation characteristics can be altered by changes in material properties (e.g. mass density and/or viscoelasticity) on or near the device surface as may be caused by sorption and/or desorption of one or more PSAs by the sensing film 16. After propagating through the sensing region, the acoustic wave is reconverted into an electrical signal by the second transducer 24b of the pair so that the modification of one or more properties of the acoustic wave (e.g. an altered or shifted frequency of oscillation) may be measured for indicating the ambient concentration of the PSAS.

The interaction of the acoustic wave with the sensing film may vary in response to an amount of the photoresist-stripping agent 100 sorbed onto or into the sensing film 16 changing a mass density and/or viscoelasticity of the film in proportion to the ambient concentration of the PSA. This interaction is manifested as a change, Δv, in the velocity of the acoustic wave traversing the sensing region, resulting in a measurable and reproducible shift, Δf, in the frequency of oscillation of the wave. The changes in velocity and frequency of the acoustic wave are interrelated as:

$$\frac{\Delta f}{f_0} = \frac{\Delta v}{v_0} = -c_m f_0 m$$

for situations where the velocity shift, Δv, is dominated by changes in the amount (i.e. the mass density per unit area, m) of the PSA sorbed by the sensing film. In the above equation, Cm is a mass sensitivity constant which depends upon the piezoelectric substrate 22 and the subscript, "0" indicates the unperturbed velocity or frequency in the absence of any sorbed PSA.

For the SAW sensor in FIG. 1, most of the energy of the acoustic wave is concentrated within about one wavelength of the surface, making the sensor very sensitive to any surface perturbations. Thus, for the SAW sensor 10, the electrode fingers are preferably spaced so as to provide a relatively high unperturbed frequency of oscillation of about 100 MHz or higher to provide a high sensitivity to a thin sensing film located on the surface of the sensor. (For a TSM sensor, the energy of a thickness shear mode therein is distributed throughout the volume of the acoustic-wave device 12 so that a thin piezoelectric crystal substrate 22 of about 0.5 millimeters thickness or less is to be preferred, since a greater fraction of the acoustic wave energy is concentrated at the surface as the substrate thickness is reduced.) To provide a chemical selectivity to a particular PSA, the sensing film 16 preferably comprises a material that selectively absorbs or adsorbs the particular PSA. For example, for measuring an ambient concentration of N-methylpyrrolidinone (also termed 1-methyl-2-pyrrolidinone or NMP) having about 0.3 torr of saturated vapor pressure at room temperature, suitable materials for forming the sensing film are poly(vinylacetate), poly (vinylphenol), poly(N-vinylpyrrolidinone) or the like.

In general, suitable materials for preparing or forming the sensing film for a particular PSA may be selected based on interactions (including acid-base interactions, hydrogen bonding, dispersion interactions, and polarity or polarizability effects) with the PSA of interest. The sensitivity and selectivity of a particular sensing film 16 will be dependent upon its chemical structure which determines its solubility properties. Thus, the greatest sensitivity for detection and monitoring of a particular PSA may be achieved by including structural elements in a film-forming material that maximize the solubility properties for the particular PSA of interest. Furthermore, suitable film-forming materials may be evaluated for use by practice of the present invention (i.e. by forming a sensing film of a candidate material that has at least a partial chemically similarity to the particular PSA to be measured) and determining a frequency shift, Δf, of the acoustic-wave sensor 10 in response to a predetermined concentration of the particular PSA. To provide a sensor 10 that responds to varying concentrations of the particular PSA, the sensing film 16 must also be capable of desorbing the PSA in response to a reduced ambient concentration of the PSA as is shown, for example, in FIG. 2.

In FIG. 1, the sensing film 16 may comprise a single thin-film layer or multiple thin-film layers. The sensing film 16 may be applied to the surface of the SAW device 12 by any deposition or coating means known to the art. A preferred method for forming the sensing film is to define the sensing region 14 photolithographically and to spin on the PSA sensing film 16 from solution after having dissolved one or more preferred film-forming materials in a solvent (e.g. acetone). The sensing film may then be dried by baking in an oven for about 10 minutes at a predetermined temperature in the range of about 60°–150° C. The sensing film formed according to this preferred method generally has a uniform layer thickness in the range of about 0.1 to 10 μm, and preferably between about 0.1 and 2 μm thickness.

In FIG. 1, electrical means 20 are connected to the acoustic-wave device 12 for activating the device to generate one or more acoustic waves 18 therein, and further for sensing or measuring the frequency shift or alteration of the acoustic waves after traversing the sensing region 14. In the preferred embodiment of the present invention in FIG. 1, the electrical means 20 includes amplifying means 26 such as a radio-frequency (rf) amplifier or the like for receiving a detected signal (including the altered or shifted frequency of oscillation) from the second transducer 24b and providing an amplified signal (i.e. a feedback signal) to the first transducer 24a at the same frequency of oscillation. By locating the acoustic-wave sensor in a feedback loop of the amplifying means as shown in FIG. 1, a free-running oscillator is formed with the frequency of oscillation changing slightly with the amount the PSA sorbed on or desorbed from the sensing film 16. In this preferred embodiment of the present invention, frequency detection means 28 such as a frequency counter or the like is connected to an output side of the amplifying means (e.g. by an rf coupler 30) for measuring the altered or shifted frequency of oscillation. The frequency detection means 28 may further include reference means (e.g. a second free-running oscillator comprising a second acoustic-wave device connected in a feedback loop of a second amplifier) for providing a reference frequency for measuring the frequency shift or alteration in response to the ambient concentration of the PSA 100. The reference frequency and the altered frequency of oscillation may be provided to a comparator or the like within the electrical means 20 for generating an output containing information about the frequency shift or the ambient concentration of the PSA determined from the frequency shift.

The electrical means 20 in this preferred embodiment of the present invention may further include other elements as known to the art including a recording device (e.g. a computer or data logger) for providing a continuous or intermittent record of the measured frequency shift (preferably converted to indicate the ambient concentration of the PSA), a readout or display device for displaying the measured PSA concentration, and a notification device for providing an alarm to indicate an ambient concentration of the PSA above a predetermined level in a particular location (e.g. a room, an IC process bay, or an exhaust stack).

Although not shown in FIG. 1, the acoustic-wave sensor 10 may further include a housing for holding the acoustic-wave sensor, and sampling means (e.g. a pump or the like) connected to the housing to provide a continuous or intermittent flow of ambient air in contact with the sensing film for sorbing the PSA 100. In some embodiments according to the present invention, the acoustic-wave sensor 10 may be packaged to provide a small, light-weight transportable monitor for one or more predetermined photoresist-stripping agents.

Additionally, temperature control means (e.g. a heating element underlying the acoustic-wave device and connected to a temperature controller having a sensing element in contact with the device 12) may be provided to control the temperature of the acoustic-wave sensor (preferably at a slightly elevated temperature of about 40° C.), to improve an accuracy of the sensor by reducing any contribution to the frequency shift, $\Delta f$, from changes in an ambient temperature.

In a second preferred embodiment of the present invention (not shown), the SAW sensor of FIG. 1 further includes reference means comprising a reference SAW device for providing a reference frequency to the frequency detection means 28 for more accurately determining a frequency shift, and for compensating for environmental factors such as temperature. The reference SAW device is preferably matched in size and construction to the acoustic-wave device 12 so that the reference SAW device responds to environmental effects (e.g. temperature) in substantially the same way that the acoustic-wave device 12 does. The reference SAW device comprises a second substrate with a second sensing region between a second pair of transducers on a surface thereof, one of the second pair of transducers generating one or more second acoustic waves at the reference frequency and the other transducer of the second pair detecting the second acoustic waves after traversing the second sensing region. The reference SAW device may further include a second sensing film in the second sensing region, in which case, the reference SAW device is preferably isolated (e.g. by a sealed enclosure or an impervious overlayer) from the ambient to prevent any contact with the PSA. Alternately, the reference SAW device may include a second sensing region that is substantially non-sorbing for a particular PSA to be sensed. Such a second sensing region may be formed either by omitting the second sensing film, or by providing a second sensing film therein that does not react with or sorb the particular PSA being sensed.

According to the second preferred embodiment of the present invention, the electrical means 20 preferably comprises amplifying means 26 such as a radio-frequency (rf) amplifier or the like connected across each of the acoustic-wave and reference SAW devices, with each SAW device forming a free-running oscillator. The electrical means 20 preferably further includes a mixer connected to the output side of each amplifying means (e.g. by an rf coupler 30) for receiving the amplified signal from each free-running oscillator and mixing the signals to generate a difference frequency output that is passed to a frequency detection means 28 such as a frequency counter or the like for measuring the difference frequency. In the absence of any ambient PSA, the difference frequency is preferably adjusted to a predetermined value (e.g. zero) so that the difference frequency provides a calibrated frequency shift for sensing an ambient concentration of PSA. In this manner, any common-mode effects (e.g. environmental effects such as temperature) that act to alter the frequencies of both the acoustic-wave device (i.e. the device sensing the PSA) and reference SAW device may be substantially nulled out to provide for a more accurate measurement of any ambient PSA.

Figure 2:
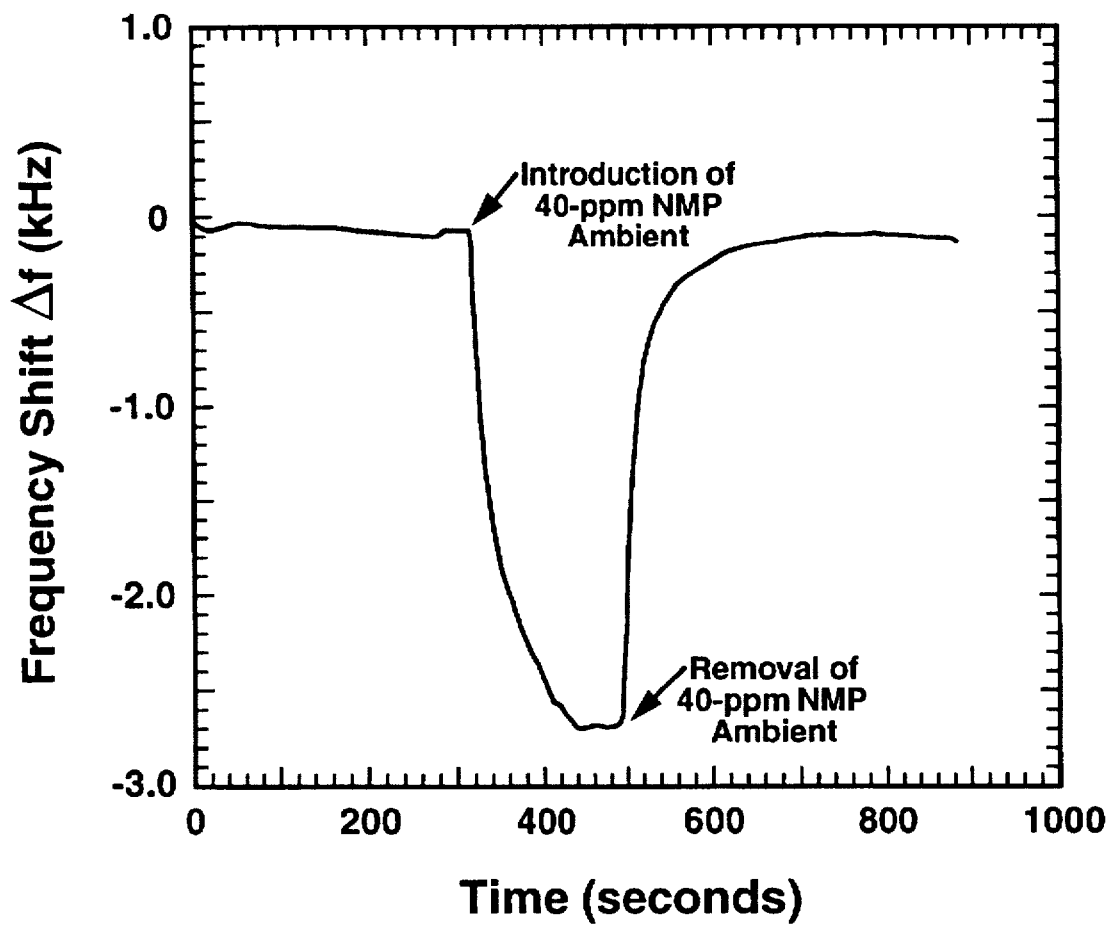
FIG. 2 shows a frequency shift versus time curve for the preferred SAW sensor embodiment of the present invention in response to a 40 part-per-million ambient concentration of a N-methylpyrrolidinone (NMP) photoresist-stripping agent.

FIG. 2 shows a frequency shift versus time curve for the preferred SAW sensor embodiment of the present invention in FIG. 1 to a 40 part-per-million (ppm) ambient concentration of an NMP photoresist-stripping agent. In FIG. 2, the sensing film comprises poly(vinylacetate). As NMP molecules are sorbed onto and into the sensing film 16, the film's mass density and viscoelasticity change in proportion to the concentration of NMP in the atmosphere contacting the film. The modification of these film properties by the sorption of NMP changes the velocity of the surface acoustic wave traversing the sensing region between the interdigital transducers resulting in a change in the frequency of oscillation of the sensor 10 which is displayed in FIG. 2.

In FIG. 2, after about 320 seconds time allotted for measuring a baseline level of the frequency shift, $\Delta f$, in the absence of any NMP photoresist-stripping agent, an ambient concentration of 40-ppm NMP is introduced to the acoustic-wave sensor with the poly(vinylacetate) sensing film. In response to the ambient NMP, the sensor produces a frequency shift of about −2.7 kHz as measured from an unperturbed frequency of about 97 MHz, indicating a sub-part-per-million (sub-ppm) detectivity for the ambient NMP photoresist-stripping agent. In FIG. 2, the SAW sensor has an equilibrium response time of about 120 seconds for measuring the 40-ppm NMP concentration. (An equilibrium response time is defined herein as a time required to reach an equilibrium state in which the frequency shift, $\Delta f$, is substantially constant after exposure to a particular concentration of a photoresist-stripping agent.) After a period of time for establishing the equilibrium response time, the ambient NMP is removed to illustrate the reversibility of the sensor response. Thus, from the curve in FIG. 2 it can be seen that the acoustic-wave sensor with a poly(vinylacetate) sensing film has an equilibrium response time that is about the same both for an exposure to an NMP ambient (i.e. sorption of NMP by the sensing film) and for recovery after removal of the NMP ambient (i.e. desorption of NMP from the sensing film).

Figure 3:
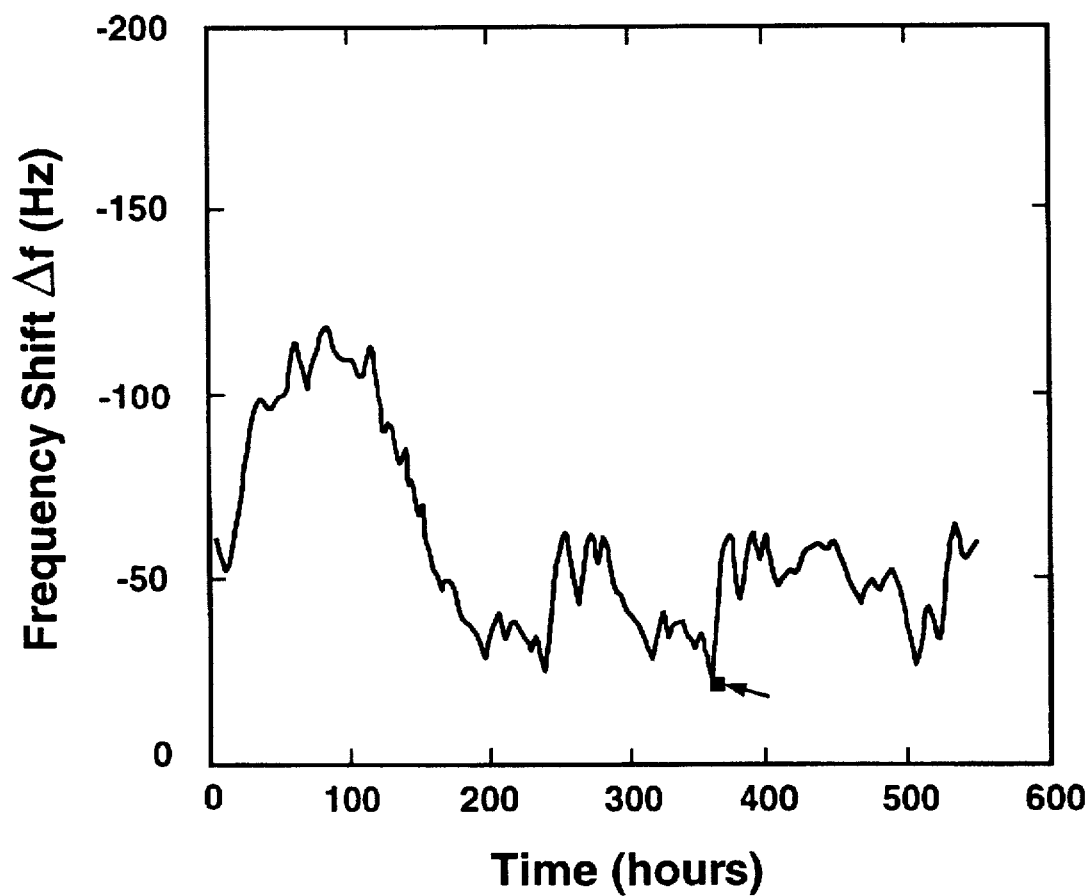
FIG. 3 shows a frequency shift versus time curve for the preferred SAW sensor embodiment of the present invention for long-term (560 hours) monitoring of NMP in the exhaust stack of a photoresist-stripping station in an IC facility.

FIG. 3 shows a frequency shift versus time curve for the preferred SAW sensor embodiment of the present invention for long-term monitoring of NMP in the exhaust stack of a photoresist-stripping station in an IC facility. For this long-term monitoring experiment, the sensing film was poly (vinylacetate). Data, collected over a time period of 560 hours, shows about a 100 Hz frequency shift, $\Delta f$, corresponding to a variation in the NMP concentration from about 0.3–1.0 part-per-million (ppm). A gas chromatography mass spectrometry (GC-MS) measurement (indicated in FIG. 3 by a solid square point as shown by the arrow) is in good agreement with the SAW sensor measurement data.

For a second SAW sensor 10 formed according to the preferred embodiment of FIG. 1, but with a poly (vinylphenol) sensing film 16, the measured frequency shift, $\Delta f$, or sensitivity of the second SAW sensor 10 for the same ambient concentration of the NMP photoresist-stripping agent is substantially larger, being about 18 kHz; and the response time for sensing the introduction of a 40-ppm ambient concentration of NMP is about the same as for the poly(vinylacetate) sensing film. However, for this second SAW sensor, the response time after removal of the NMP ambient is much longer. A third SAW sensor 10 having a poly(N-vinylpyrrolidinone) sensing film shows a sensitivity that is smaller than that for the second sensor; but with similar response times after introduction and removal of the NMP ambient. For yet a fourth SAW sensor without any PSA sensing film, the frequency shift, $\Delta f$, remains substantially unchanged after exposure to the 40-ppm NMP ambient, thereby showing the necessity for providing the sensing film 16 (and the possibility for forming a reference SAW sensor by omitting the PSA sensing film).

In other embodiments of the present invention, measurements of an amplitude of the detected and feedback signals may be used to provide an indication of an attenuation in the acoustic wave 18 as it traverses the sensing region 14 as disclosed in U.S. Pat. No. 5,076,094 which is incorporated herein by reference. The attenuation is independent of the mass of the sorbed PSA; and is instead dependent upon an alteration in properties of the sensing film 16. Therefore, a measurement of the attenuation of the acoustic wave in combination with the frequency alteration or shift may provide further selectivity for determining a particular PSA, or for discriminating against ambient concentrations of other non-PSA chemical species (e.g. volatile organic species).

There has thus been shown an acoustic-wave sensor for measuring an ambient concentration of one or more photoresist-stripping agents. The matter set forth in the foregoing description and accompanying drawings is offered by way of illustration only and not as a limitation. Other applications and variations of the acoustic-wave sensor will become evident to those skilled in the art. For example, although the invention has been disclosed in terms of preferred acoustic-wave SAW sensors, the acoustic-wave sensor may be formed of any type of acoustic-wave device including flexural-plate-wave devices, acoustic-plate-mode devices and thickness-shear-mode devices (also termed quartz crystal microbalances). The actual scope of the invention is intended to be defined in the following claims when viewed in their proper perspective based on the prior art.

What is claimed is:

1. An acoustic-wave sensor for measuring an ambient concentration of a low-volatility photoresist-stripping agent comprising;
   an acoustic-wave device having a sensing region on a surface thereof, the sensing region including a photoresist-stripping-agent sensing film;
   a housing for holding the acoustic-wave sensor: and
   sampling means for providing a flow of ambient air in contact with the sensing film for sorbing a quantity of the low-volatility photoresist-stripping agent and thereby altering a frequency of an acoustic wave propagating through the sensing region, the altered frequency providing an indication of the ambient concentration of the photoresist-striping agent.

2. The acoustic-wave sensor of claim 1 wherein the acoustic-wave device includes at least one transducer for generating or detecting the acoustic wave.

3. The acoustic-wave sensor of claim 1 further including means connected to the acoustic-wave device for generating the acoustic wave, and for sensing the altered frequency thereof.

4. The acoustic-wave sensor of claim 3 wherein the electrical means in combination with the acoustic-wave device forms a free-running oscillator, with the acoustic-wave device being connected in a feedback loop of the oscillator.

5. The acoustic-wave sensor of claim 1 wherein the acoustic-wave device is selected from the group consisting of surface-acoustic-wave devices, flexural-plate-wave devices, acoustic-plate-mode devices and thickness-shear mode devices.

6. The acoustic-wave sensor of claim 3 further including a reference acoustic-wave device for providing a reference frequency to the electrical means.

7. The acoustic-wave sensor of claim 6 wherein the reference acoustic-wave device is isolated from contact with the photoresist-stripping agent.

8. The acoustic-wave sensor of claim 6 wherein the reference acoustic-wave device includes a reference sensing region that is substantially non-sorbing of the low-volatility photoresist-stripping agent.

9. The acoustic-wave sensor of claim 1 wherein the low-volatility photoresist-stripping agent is selected from the group consisting of N-methylpyrrolidinone (NMP) and ethoxyethylpropionate (EEP).

10. The acoustic-wave sensor of claim 9 wherein the sensing film is selected from the group consisting of poly (vinylacetate), poly(N-vinylpyrrolidinone), and poly (vinylphenol).

11. An acoustic-wave sensor for measuring an ambient concentration of a low-volatility photoresist-stripping agent comprising:
   (a) a surface-acoustic-wave (SAW) device having a pair of interdigitated transducers with a plurality of fingers thereof spaced apart on a quartz substrate and further including on the substrate between the transducers a sensing region including a sensing film for sorbing at least a part of the low-volatility photoresist-stripping agent;
   (b) housing for holding the SAW device;
   (c) sampling means for providing a flow of ambient air in contact with the sensing film for sorbing the low-volatility photoresist-striping agent; and
   (d) electrical means connected to the transducers for activating the transducers and measuring a frequency of a surface acoustic wave propagating between the transducers, the frequency being shifted in response to sorption of the photoresist-striping agent, with the frequency shift providing an indication of the ambient concentration of the low-volatility photoresist-stripping agent.

12. The acoustic-wave sensor of claim 11 wherein the electrical means in combination with the SAW device forms a free-running oscillator, with the SAW device being connected in a feedback loop of the oscillator.

13. The acoustic-wave sensor of claim 11 further including a reference SAW device for providing a reference frequency to the electrical means.

14. The acoustic-wave sensor of claim 11 wherein the low-volatility photoresist-stripping agent is selected from the group consisting of N-methylpyrrolidinone (NMP) and ethoxyethylpropionate (EEP).

15. The acoustic-wave sensor of claim 14 wherein the sensing film is selected from the group consisting of poly (vinylacetate), poly(N-vinylpyrrolidinone), and poly (vinylphenol).

* * * * *